(12) United States Patent
Hsieh et al.

(10) Patent No.: US 12,114,751 B2
(45) Date of Patent: Oct. 15, 2024

(54) NAIL FILING MACHINE, UV LIGHT STERILIZATION CONTAINER, AND NAIL FILING SYSTEM INCLUDING THE NAIL FILING MACHINE

(71) Applicant: COSMEX CO., LTD., New Taipei (TW)

(72) Inventors: Wan-Chieh Hsieh, New Taipei (TW); Pai-Yao Hsieh, New Taipei (TW); Chien-Chieh Tung, New Taipei (TW)

(73) Assignee: COSMEX CO., LTD., New Taipei (TW)

( * ) Notice: Subject to any disclaimer, the term of this patent is extended or adjusted under 35 U.S.C. 154(b) by 1003 days.

(21) Appl. No.: 17/039,651

(22) Filed: Sep. 30, 2020

(65) Prior Publication Data
US 2021/0100332 A1 Apr. 8, 2021

(30) Foreign Application Priority Data
Oct. 5, 2019 (TW) ................................ 108214367

(51) Int. Cl.
*A45D 29/05* (2006.01)
*A61L 2/10* (2006.01)

(52) U.S. Cl.
CPC ................ *A45D 29/05* (2013.01); *A61L 2/10* (2013.01); *A61L 2202/122* (2013.01); *A61L 2202/16* (2013.01)

(58) Field of Classification Search
CPC ........ A45D 29/00; A45D 29/05; A45D 29/06; A45D 29/14; A45D 29/17; A45D 29/18; A45D 29/20; A61L 2/10; A61L 2/26; A61L 2202/16; A61L 2202/122; A61B 17/54; A61B 2017/00398; G08C 17/02; G08C 2201/30; H02J 7/0045; H02J 7/0047; H02J 7/0044
USPC ...... 132/73.6, 75.8, 76.4, 73, 73.5, 75.6, 75, 132/76.5, 75.3, 200
See application file for complete search history.

(56) References Cited

U.S. PATENT DOCUMENTS

| | | | |
|---|---|---|---|
| 2008/0216647 A1* | 9/2008 | Phan ........................ | A61L 9/16 108/50.13 |
| 2011/0174859 A1* | 7/2011 | Zhou ...................... | B25C 1/184 227/144 |
| 2013/0092182 A1* | 4/2013 | Stockbauer ............ | A45D 29/05 132/75.8 |
| 2015/0173484 A1* | 6/2015 | Fitzsimons ............ | A45D 29/05 132/200 |
| 2015/0289627 A1* | 10/2015 | Chang .................... | A45D 29/00 34/275 |
| 2018/0042802 A1* | 2/2018 | St. Louis ............. | A61C 1/0023 |

(Continued)

*Primary Examiner* — Cris L. Rodriguez
*Assistant Examiner* — Karim Asqiriba
(74) *Attorney, Agent, or Firm* — MUNCY, GEISSLER, OLDS & LOWE, P.C.

(57) ABSTRACT

The present invention relates to a nail filing machine, an ultraviolet (UV) light sterilization container, and a nail filing system including the nail filing machine. The nail filing machine of the present invention comprises a pen-shaped nail filing device, a master device and a rotation speed-adjustable motor. The nail filing machine of the present invention is convenient for a user (i.e., a manicurist) to use for a long time, is easy to carry in use, has a UV light sterilization function, and can record the working mode of the user, thereby effectively improving the operability of the nail filing machine.

34 Claims, 9 Drawing Sheets

(56) References Cited

U.S. PATENT DOCUMENTS

| | | | |
|---|---|---|---|
| 2019/0117356 A1* | 4/2019 | Bärtschi | A46B 9/026 |
| 2019/0380471 A1* | 12/2019 | Peleg-Turgeman | A45D 29/00 |
| 2020/0052514 A1* | 2/2020 | Haile | A45D 29/05 |
| 2020/0375336 A1* | 12/2020 | Hurter | H02J 7/0044 |
| 2021/0045513 A1* | 2/2021 | Cheng | H02J 7/0045 |
| 2023/0134504 A1* | 5/2023 | Haile | A45D 29/05 132/73.6 |
| 2024/0000211 A1* | 1/2024 | Su | A45D 29/05 |

* cited by examiner

NAIL FILING MACHINE, UV LIGHT STERILIZATION CONTAINER, AND NAIL FILING SYSTEM INCLUDING THE NAIL FILING MACHINE

BACKGROUND OF THE INVENTION

1. Technical Field

The present invention relates to a nail filing machine, an ultraviolet (UV) light sterilization container, and a nail filing system including the nail filing machine, and more particularly to a multifunctional nail filing machine, a UV light sterilization container, and a nail filing system including the nail filing machine.

2. Description of Related Art

Nail filing machines are typically used in manicures to file, trim, buff, and adjust the shape of nails (including hard nails) so that nail polish can be evenly and smoothly applied over the nail surface to facilitate painting on the nails and adhesive attachment of nail decorations, such as glittering beads. Nail filing machines are indispensable to manicurists because they can satisfy consumers' manicure requirements by achieving a higher level of delicacy in manicure than when they are not used. The market has been supplied with a great variety of nail filing machines, in which compact, quiet, low-vibration, and stylish models are generally preferred.

Nail filing machines provide improvements over the use of the conventional nail files, which tend to scratch the nail being filed or the skin nearby because it is difficult to control the force applied through, and the angle of, such a file during the filing process. Moreover, a nail filing machine may be provided with grinding members of different configurations for selective use.

BRIEF SUMMARY OF THE INVENTION

Nail filing machines are effective in enhancing the process of nail beautification but are inconvenient in that the time required for filing is usually long (e.g., the removal of artificial nails often takes more than half an hour), and that the grinding members must be sterilized after use in order to be used on the next consumer. The aforesaid inconveniences need to be addressed.

In order to solve the above problem, the present invention is to provide a nail filing machine comprising a pen-shaped nail filing device, a master device and a rotation speed-adjustable motor. The pen-shaped nail filing device includes a handle housing and a main shaft provided in the handle housing, wherein the main shaft is provided with a closable clamping member. The master device is separate from or co-constructed with the pen-shaped nail filing device, wherein the master device is connected or coupled to the pen-shaped nail filing device by an electrical connection means, and the master device includes a control unit. The rotation speed-adjustable motor is provided in the handle housing or the master device, wherein the rotation speed-adjustable motor is connected or coupled to the main shaft in order to drive the main shaft into rotation. The control unit adjusts a working mode of the pen-shaped nail filing device according to a corresponding control instruction.

In a preferred embodiment, the pen-shaped nail filing device includes a grinding unit mounted on the closable clamping member.

In a preferred embodiment, the rotation speed-adjustable motor is a bi-directional motor whose rotation direction is switched on an instruction of the control unit.

In a preferred embodiment, the handle housing is provided with a rotating member, wherein the closable clamping member is closed when the rotating member is turned in a direction, and the closable clamping member is opened when the rotating member is turned in an opposite direction.

In a preferred embodiment, the handle housing includes a handle portion and a front housing portion joined to a front end of the handle portion, and the front housing portion has a front end having an opening through which a grinding unit can be passed.

In a preferred embodiment, the handle housing has an outer side provided with an anti-sliding member.

In a preferred embodiment, the anti-sliding member is an anti-sliding pattern, an anti-sliding sleeve, or an anti-sliding material.

In a preferred embodiment, the handle housing is provided with a heat dissipation device corresponding in position to the rotation speed-adjustable motor.

In a preferred embodiment, the master device inputs a corresponding rotation speed modulation instruction to the control unit of the master device through a human-machine interface so as to control the working mode, and the working mode includes rotation speed and rotation direction of the rotation speed-adjustable motor.

In a preferred embodiment, the human-machine interface is a multi-step/stepless turning knob, a geared knob, a control dial, a translational push lever, a wired or wireless transmission pedal, a touchpad, touch screen, touch button, press keys, a microphone, a multi-step/stepless trigger, or a multi-step/stepless regulation pushbutton.

In a preferred embodiment, the master device is provided with a clip on one side.

In a preferred embodiment, the master device includes a rechargeable battery and/or a power supply unit that is connected or coupled to the control unit in order to provide the control unit with electricity required for its operation.

In a preferred embodiment, the master device includes a display unit displaying at least one indication selected from a group of rotation speed, operation time, remaining power level, load, forward/reverse rotation, temperature, and line connection state.

In a preferred embodiment, the nail filing machine further includes a base where the master device can be placed.

In a preferred embodiment, the base has a bottom side provided with one or more anti-sliding pads or non-slip structures.

In a preferred embodiment, the base is provided with a power supply to be connected to an external power source and a power providing unit connected to the power supply, and the power providing unit is connected or coupled to a power port of the master device in order to provide the rechargeable battery and/or the power supply unit with required electricity.

In a preferred embodiment, the master device includes a timer for recording a working time of the rechargeable battery in order for the control unit to calculate a remaining service life of the rechargeable battery according to the working time of the rechargeable battery or a number of times of charging and discharge.

In a preferred embodiment, the base is provided with one or more expansion ports, and the power supply is connected or coupled to the one or more expansion ports in order to supply electricity thereto.

In a preferred embodiment, the base is provided with a placement hole where a grinding unit can be placed.

In a preferred embodiment, the electrical connection means is conductive wires, coiled conductive wires, a cable box and its conductive wires, a circuit board, or a transmission cable.

In a preferred embodiment, the handle housing of the pen-shaped nail filing device or the master device is provided therein with a rotation speed detection unit, or the rotation speed detection unit is co-constructed with the rotation speed-adjustable motor instead; wherein the rotation speed detection unit is connected or coupled to the control unit in order to send a rotation speed parameter of the pen-shaped nail filing device to the control unit as feedback.

In a preferred embodiment, the control unit includes a storage unit; the control unit sets a working mode for the pen-shaped nail filing device; wherein, the working mode comprises a manual control instruction in a manual setting list, a recorded control instruction in a frequently-used-parameter list, or a default control instruction in the storage unit; wherein, the manual control instruction in the manual setting list is set from the control unit according to an instruction input through a human-machine interface in order to record the manual control instruction into the storage unit, the recorded control instruction in the frequently-used-parameter list is recorded by the control unit with a rotation speed parameter when a working time of a certain rotation speed parameter exceeds a preset value, and the default control instruction is a preset control instruction already stored in the storage unit.

In a preferred embodiment, the master device includes a timer for recording a working time of the rotation speed-adjustable motor.

In a preferred embodiment, the handle housing of the pen-shaped nail filing device or the master device is provided therein with a temperature detection unit, or the temperature detection unit is co-constructed with the rotation speed-adjustable motor instead; wherein the temperature detection unit is connected or coupled to the control unit in order to send a temperature parameter of the pen-shaped nail filing device to the control unit as feedback.

In a preferred embodiment, the handle housing of the pen-shaped nail filing device or the master device is provided therein with a load detection unit, or the load detection unit is co-constructed with the rotation speed-adjustable motor instead; wherein the load detection unit is connected or coupled to the control unit in order to send a load parameter of the pen-shaped nail filing device to the control unit as feedback.

In a preferred embodiment, the handle housing of the pen-shaped nail filing device or the master device is provided therein with a dust detection unit, and the dust detection unit is connected or coupled to the control unit in order to send a dust amount parameter of the pen-shaped nail filing device to the control unit as feedback.

In a preferred embodiment, the handle housing of the pen-shaped nail filing device is provided therein with a connection detection unit, or the connection detection unit is provided in the master device instead; wherein the connection detection unit is connected or coupled to the control unit in order to send an electrical parameter between circuits of interest to the control unit as feedback, thereby allowing the control unit to derive a line connection state from the electrical parameter.

Another objective of the present invention is to provide an ultraviolet (UV) light sterilization container comprising a housing, a power source module, at least one UV light emitting unit, and a control module. The housing has a receiving space, wherein the receiving space is provided therein with a placement unit where a grinding unit is able to be placed. The power source module is for providing electricity. The at least one UV light emitting unit is provided in the receiving space. The control module is connected to the power source module and the UV light emitting unit, wherein the control module controls output of the UV light emitting unit through a control instruction.

In a preferred embodiment, the UV light sterilization container further includes a rechargeable battery connected to the power source module and the control module.

In a preferred embodiment, the UV light sterilization container is set in cooperation with the above-mentioned nail filing machine, and the housing is co-constructed with the master device or is electrically connected to the master device of the nail filing machine via a conductive wire.

In a preferred embodiment, the UV light sterilization container is set in cooperation with the above-mentioned nail filing machine, and the housing is co-constructed with the base or the master device of the nail filing machine or is connected to the base or the master device of the nail filing machine.

In a preferred embodiment, the housing has one or a plurality of reflective surfaces or reflective units on an inner side facing the receiving space.

In a preferred embodiment, the housing is made of a photochromic material with a normal transparent or translucent state and a UV-blocking state that takes place when the UV light emitting units are activated.

In a preferred embodiment, the housing includes a main body portion and a cover that is pivotally provided on the main body portion via an elastic opening/closing means.

In a preferred embodiment, the cover is pivotally provided on the main body portion through a damper unit.

Another objective of the present invention is to provide a nail filing system comprising the above-mentioned nail filing machine and a mobile device. The nail filing machine further includes a first transmission unit connected to the control unit. The mobile device is connected to the first transmission unit of the nail filing machine through a transmission means in order to access data in the control unit through the first transmission unit.

In a preferred embodiment, the handle housing of the pen-shaped nail filing device or the master device is provided therein with a rotation speed detection unit, or the rotation speed detection unit is co-constructed with the rotation speed-adjustable motor instead; wherein the rotation speed detection unit is connected or coupled to the control unit in order to send a rotation speed parameter of the pen-shaped nail filing device to the control unit as feedback, and the mobile device obtains the rotation speed parameter of the rotation speed-adjustable motor through the control unit.

In a preferred embodiment, the master device includes a timer for recording a working time of the rotation speed-adjustable motor, and the mobile device obtains the working time of the rotation speed-adjustable motor through the control unit and stores the working time into the work history database in the storage unit of the mobile device.

In a preferred embodiment, the handle housing of the pen-shaped nail filing device or the master device is provided therein with a temperature detection unit, or the temperature detection unit is co-constructed with the rotation speed-adjustable motor instead; wherein the temperature detection unit is connected or coupled to the control unit in order to send a temperature parameter of the pen-shaped nail filing device to the control unit as feedback, and the mobile device obtains the temperature parameter of the rotation speed-adjustable motor in a working state through the control unit and stores the temperature parameter into the work history database in the storage unit of the mobile device.

In a preferred embodiment, the handle housing of the pen-shaped nail filing device or the master device is provided therein with a load detection unit, or the load detection unit is co-constructed with the rotation speed-adjustable motor instead; wherein the load detection unit is connected or coupled to the control unit in order to send a load parameter of the pen-shaped nail filing device to the control unit as feedback, or the mobile device obtains the load parameter of the rotation speed-adjustable motor in a working state through the control unit.

In a preferred embodiment, the handle housing of the pen-shaped nail filing device or the master device is provided therein with a dust detection unit, the dust detection unit is connected or coupled to the control unit in order to send a dust amount parameter of the pen-shaped nail filing device to the control unit as feedback, or the mobile device obtains the dust amount parameter through the control unit and, when the dust amount parameter exceeds a preset value, outputs a notification signal through the screen or the loudspeaker of the mobile device.

In a preferred embodiment, the handle housing is provided therein with a connection detection unit, or the connection detection unit is provided in the master device instead; wherein the connection detection unit is connected or coupled to the control unit in order to send an electrical parameter between circuits of interest to the control unit as feedback, thereby allowing the control unit to derive a line connection state from the electrical parameter, or the mobile device obtains the line connection state through the control unit and, when the line connection state is an improper connection state, outputs a notification signal through the screen or the loudspeaker of the mobile device.

In a preferred embodiment, the control unit of the pen-shaped nail filing device comprises a programmable controller, the mobile device provides a modification platform to a human-machine interface of the mobile device through a mobile application program installed in a processor of the mobile device, and the processor outputs a programming instruction according to an instruction input through the modification platform and sends the programing instruction to the control unit of the nail filing machine by a transmission means in order to modify procedures of the control unit.

In summary, the present invention aims to provide a multifunctional nail filing machine, an ultraviolet (UV) light sterilization container, and a nail filing system including the nail filing machine. It is desirable that the nail filing machine can record a user's use habit and perform various functions so as to provide much better user experience than the prior art.

DETAILED DESCRIPTION OF THE INVENTION

The details and technical solution of the present invention are hereunder described with reference to accompanying drawings. For illustrative sake, the accompanying drawings are not drawn to scale. The accompanying drawings and the scale thereof are not restrictive of the invention.

A preferred embodiment of the nail filing machine of the present invention is described below with reference to FIG. 1 to FIG. 4, which respectively show a first perspective view, a second perspective view, and an exploded view of the nail filing machine of the invention and a perspective view of an integral assembly of the master device and the pen-shaped nail filing device of the nail filing machine of the invention in a pen-shaped co-constructed configuration.

Figure 1:
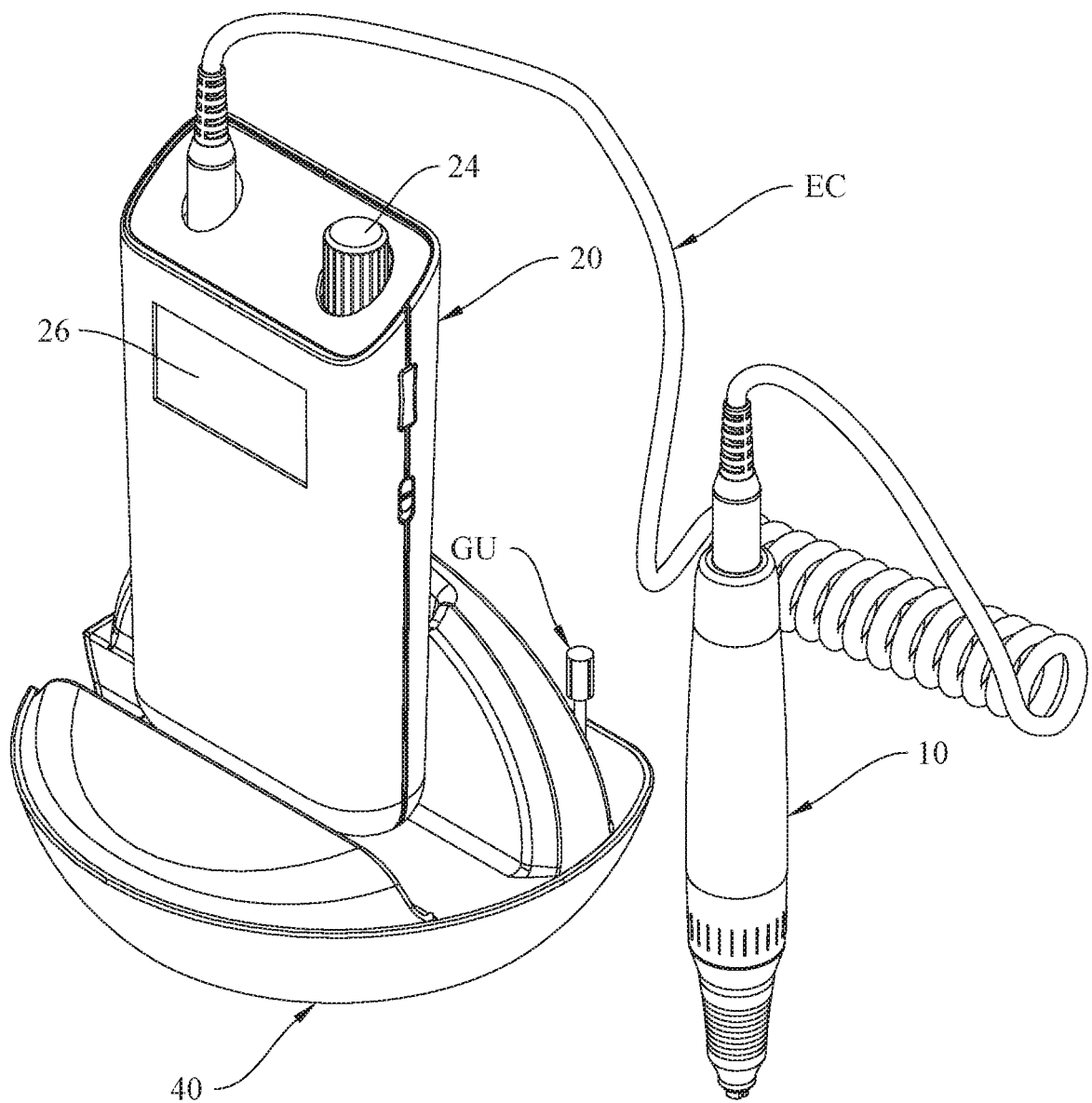
FIG. 1 is a first perspective view of the nail filing machine of the present invention.
Figure 2:
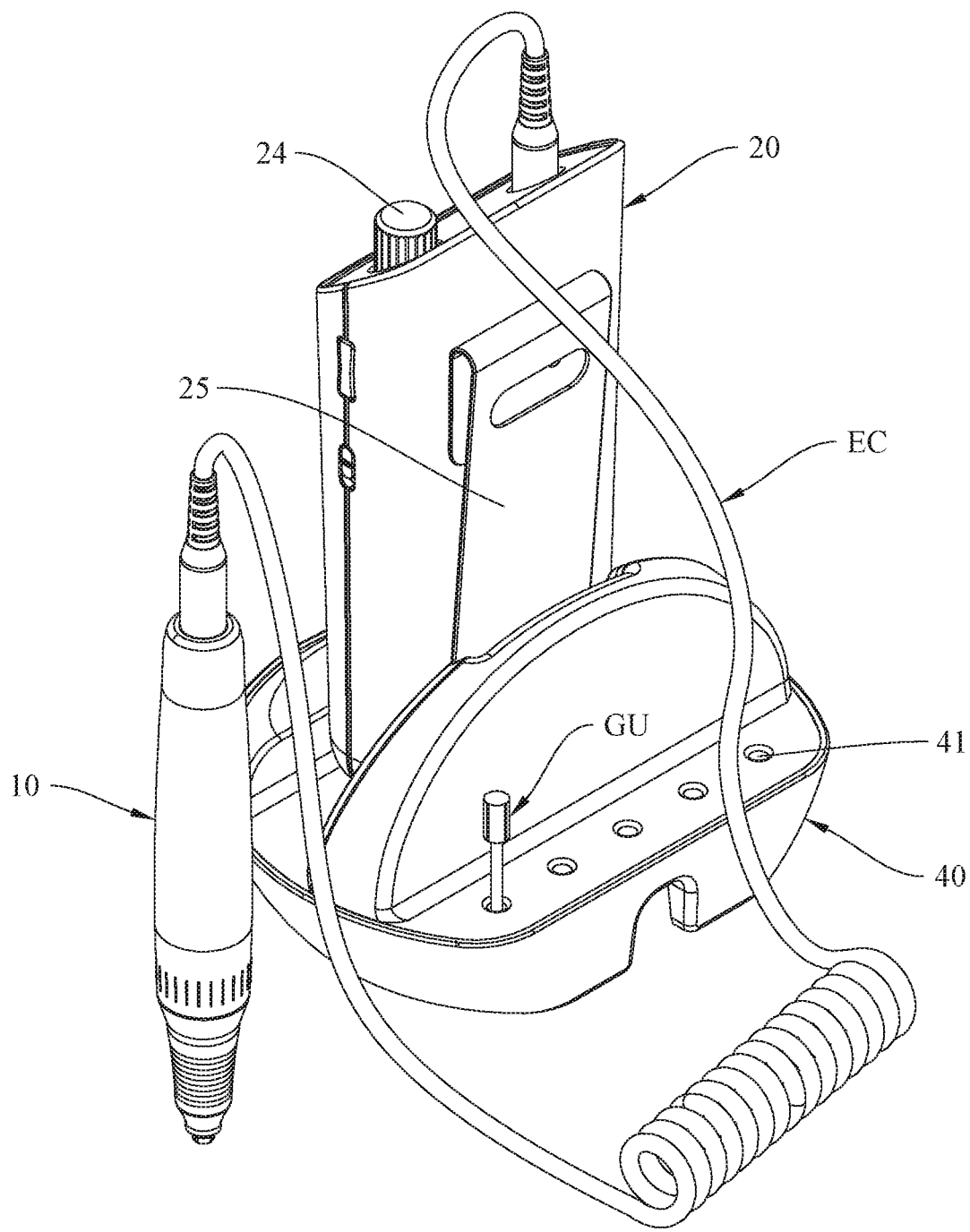
FIG. 2 is a second perspective view of the nail filing machine of the present invention.
Figure 3:
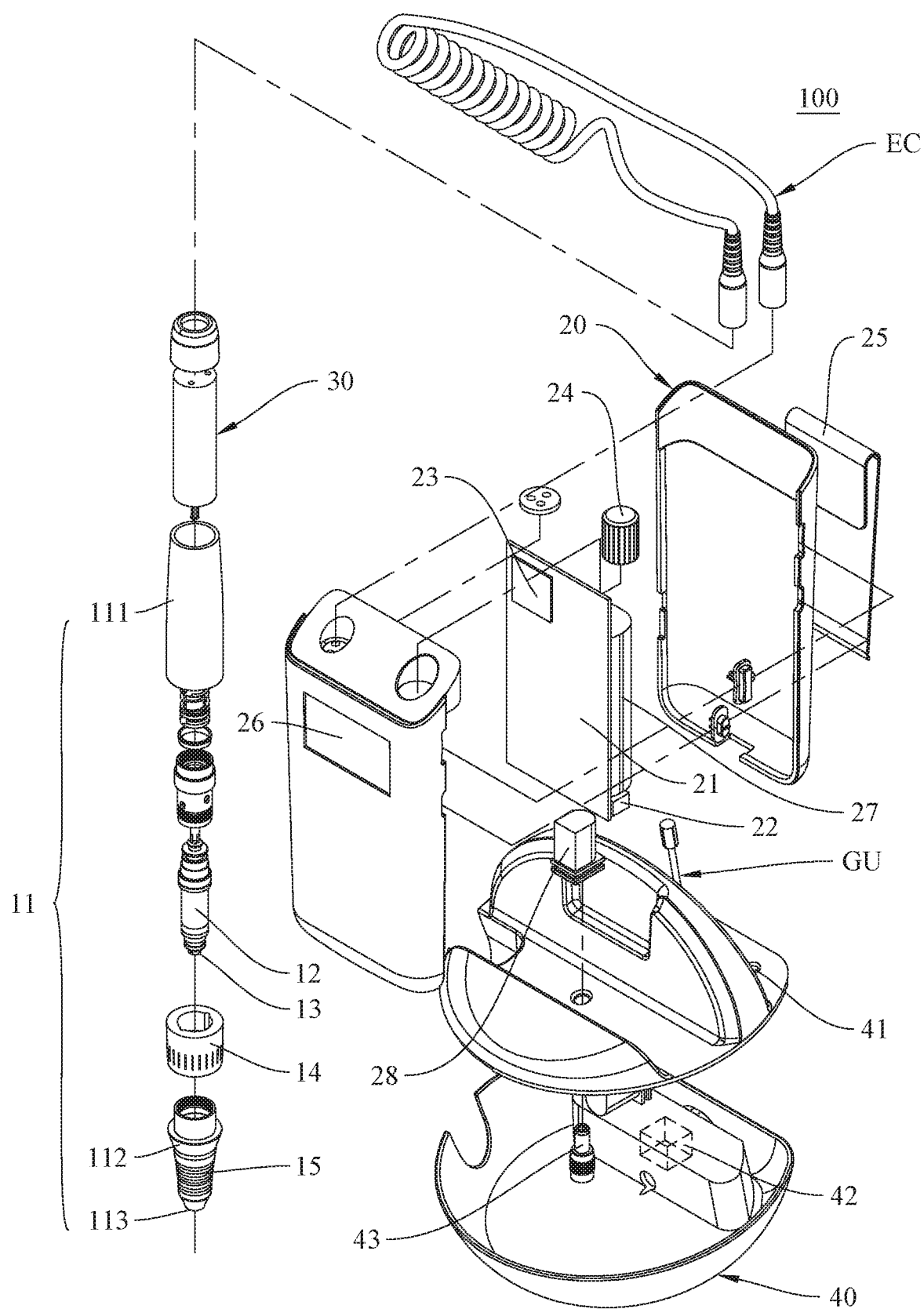
FIG. 3 is an exploded view of the nail filing machine of the present invention.
Figure 4:
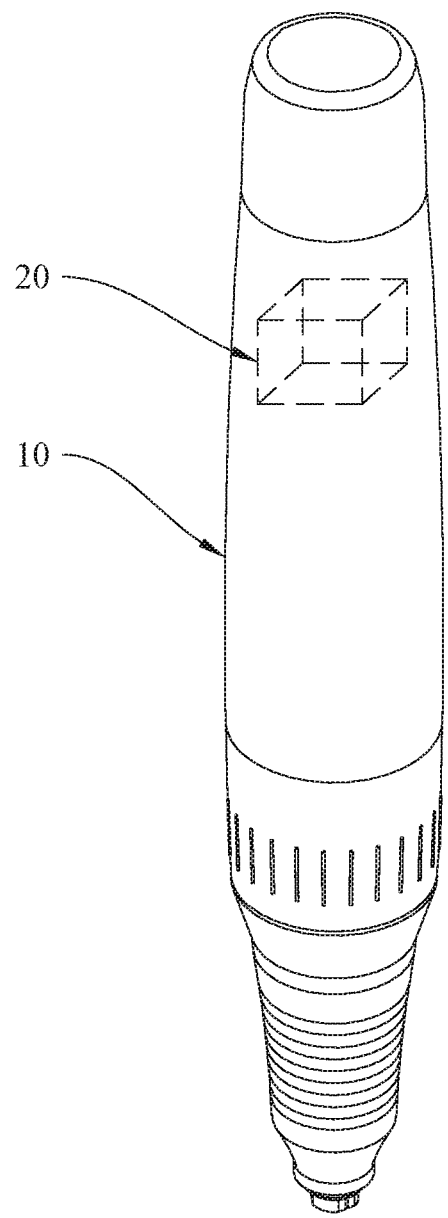
FIG. 4 is a perspective view of an integral assembly of the master device and the pen-shaped nail filing device of the nail filing machine of the present invention in a pen-shaped co-constructed configuration.

The nail filing machine 100 in this embodiment essentially includes a pen-shaped nail filing device 10, a master device 20 connected to the pen-shaped nail filing device 10, and a motor 30 whose rotation speed can be adjusted (hereinafter referred to as the rotation speed-adjustable motor 30). In one feasible embodiment, the pen-shaped nail filing device 10 is separate from, and can be maneuvered independently of, the master device 20, as shown in FIG. 1 to FIG. 3. In another feasible embodiment, the electronic components of the master device 20 are integrated and then co-constructed with the pen-shaped nail filing device 10 to form an integral pen-shaped design, as shown in FIG. 4. The present invention has no limitation on whether the pen-shaped nail filing device 10 and the master device 20 are co-constructed or otherwise.

The pen-shaped nail filing device 10 essentially includes a handle housing 11 and a main shaft 12 provided in the handle housing 11. A closable clamping member 13 is provided at the main shaft 12 and can be opened and closed in order to have a grinding unit GU mounted therein or removed therefrom, thereby allowing replacement of the grinding unit GU.

The master device 20 is connected or coupled to the pen-shaped nail filing device 10 by an electrical connection means EC and is configured to control the pen-shaped nail filing device 10 or provide the driving power needed by the pen-shaped nail filing device 10. The master device 20 includes a control unit 21, and the control unit 21 is configured to adjust the working mode of the pen-shaped nail filing device 10 according to a corresponding control instruction. The control unit 21 comprises a programmable general- or special-purpose microprocessor, a digital signal processor, a programmable controller, an application-specific integrated circuit, a programmable device, other similar devices, or a combination of the above; the present invention has no limitation in this regard.

The control unit 21 includes a storage unit. The control unit 21 sets a working mode for the pen-shaped nail filing device 10 and the working mode comprises a manual control instruction in a manual setting list, a recorded control instruction in a frequently-used-parameter list, or a default control instruction in the storage unit. The manual control instruction in the manual setting list is set from the control unit 21 according to an instruction input through a human-machine interface in order to record the manual control instruction into the storage unit; in other words, a user may set a working mode of the pen-shaped nail filing device 10 through a human-machine interface into the control unit 21 as an entry in a manual setting list, with the control unit 21 storing the manual setting list in the storage unit. The recorded control instruction in the frequently-used-parameter list is recorded by the control unit 21 with a rotation speed parameter when a working time of a certain rotation speed parameter exceeds a preset value. The default control instruction is a preset control instruction already stored in the storage unit.

The rotation speed-adjustable motor 30 is configured to drive the main shaft 12 of the pen-shaped nail filing device 10, and hence the grinding unit GU in use, into rotation in order to perform such functions as nail filing, nail trimming, nail buffing, nail shape adjustment, and hard nail cutting. In one feasible embodiment, the rotation speed-adjustable motor 30 is directly provided in the handle housing 11 of the pen-shaped nail filing device 10 and is connected to the main shaft 12 either directly or through a linking mechanism (e.g., a bushing or gear). In another feasible embodiment, the rotation speed-adjustable motor 30 may be provided in the master device 20 instead and be coupled to the main shaft 12 via a line-based transmission mechanism (e.g., a transmission cable). The present invention has no limitation on the location of the rotation speed-adjustable motor 30 or how the rotation speed-adjustable motor 30 is connected or coupled to the main shaft 12. In one preferred embodiment, the rotation speed-adjustable motor 30 is a bi-directional motor whose rotation direction is switched on the instruction of the control unit 21. The invention, however, has no limitation on the type of the rotation speed-adjustable motor 30 either.

Figure 5:
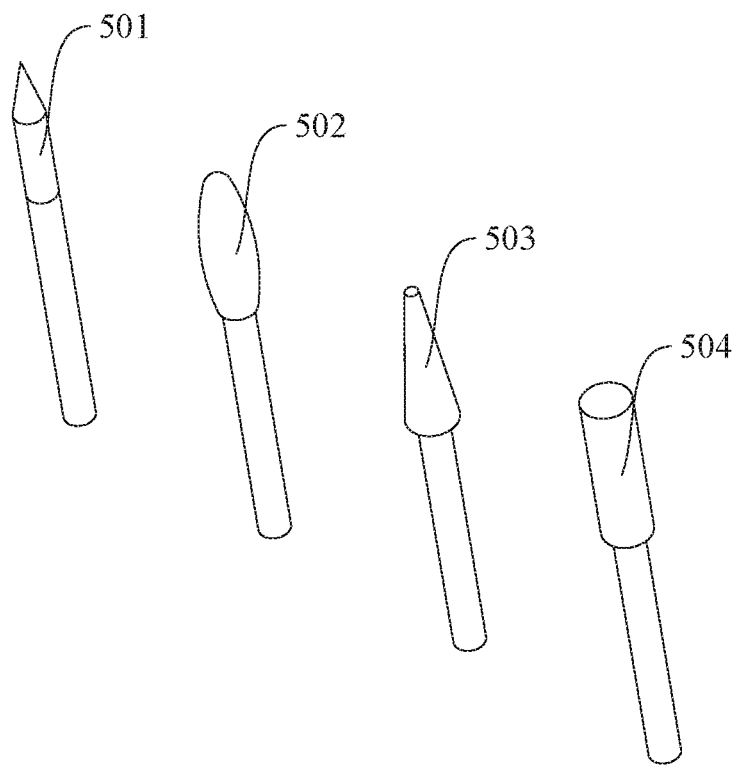
FIG. 5 is a schematic diagram of appearance of grinding units in the present invention.
Figure 6A:
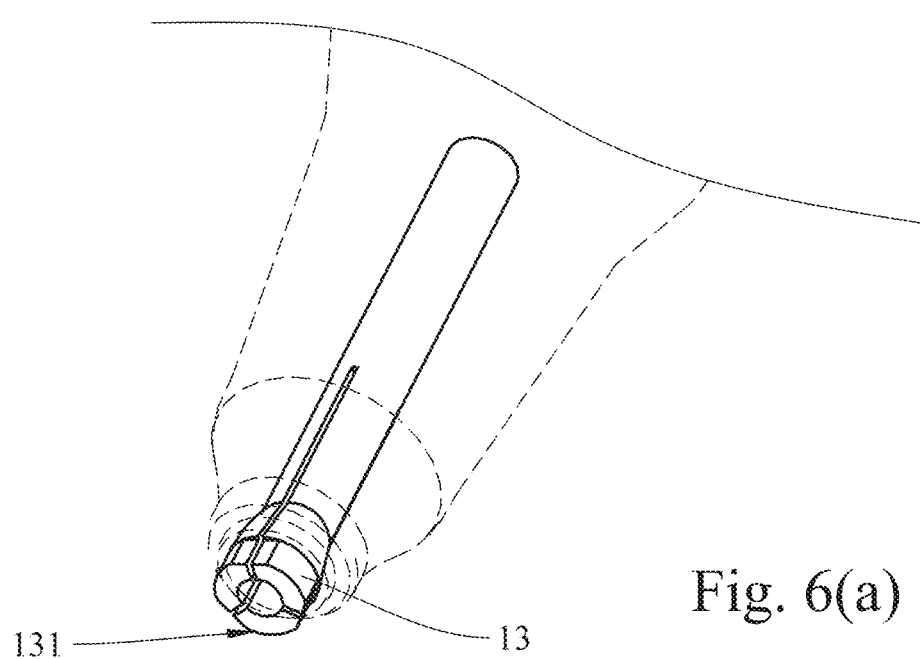
FIG. 6 is an operation diagram in the closable clamping member of the present invention.

Please refer to FIG. 5 and FIG. 6, which show the looks of a few grinding units for use in the present invention and how the closable clamping member works.

As shown in FIG. 5, the grinding units GU in one feasible embodiment have different model numbers and can be swapped for one another according to different nail filing needs. The grinding units may include, but are not limited to, a needle-shaped grinding member 501, a bullet-shaped grinding member 502, a conical grinding member 503, and a cylindrical grinding member 504. The needle-shaped grinding member 501 can be used to carve a nail or file the edge of a nail. The bullet-shaped grinding member 502 can be used to grind and thereby flatten the protuberances on a nail or remove an artificial nail. The conical grinding member 503 can be used to grind a newly trimmed nail edge into a smoothly curved shape. The cylindrical grinding member 504 can be used to file a nail, grind the base of a nail, remove the thickened dead skin or callus around a nail, or remove an artificial nail.

Referring to FIG. 6, the closable clamping member 13, which is at the main shaft 12, can be opened and closed through mechanism adjustment such that the size of the opening formed by the claws 131 of the closable clamping member 13 is changed. While there are three claws 131 in this embodiment, there may be two, four, or more claws 131 instead. The spacing between the claws 131 defines the aforesaid opening, so the size of the opening can be adjusted by changing the spacing between the claws 131 in order to lock a grinding unit GU tightly in place.

Figure 6B:
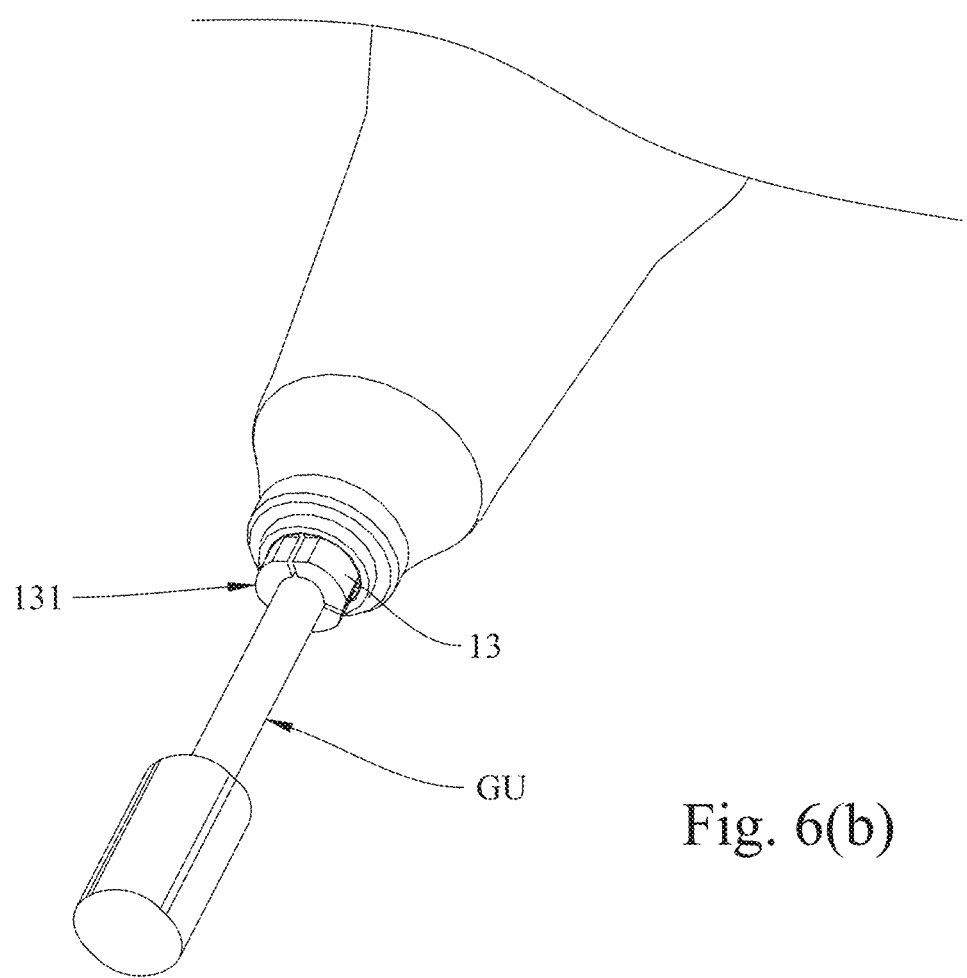

To open and close the claws 131, referring back to FIG. 3, a rotating member 14 is provided on the handle housing 11. When the rotating member 14 is turned in a certain direction, the corresponding mechanism in the handle housing 11 is compressed and thus pushes the claws 131 in a first direction, and when pushed in the first direction, the claws 131 are forced to close by a position-limiting mechanism (e.g., an inclined groove) at the opening of the handle housing 11; as a result, the claws 131 of the closable clamping member 13 are brought closer to one another to clamp a grinding unit GU tightly in place, as shown in FIG. 6(b). Conversely, when the rotating member 14 is turned in the opposite direction, the corresponding mechanism in the handle housing 11 moves the claws 131 in a second direction, and when moved in the second direction, the claws 131 are gradually driven away from the position-limiting side to the releasing side of the position-limiting mechanism (e.g., an inclined groove); as a result, the claws 131 of the closable clamping member 13 are loosened and can be moved further apart from one another to allow replacement of the grinding unit GU.

In one feasible embodiment, the nail filing machine 100 includes a base 40 where the master device 20 can be placed. To prevent the base 40 from sliding on a flat surface, the bottom side of the base 40 is provided with one or a plurality of anti-sliding structures (not shown), such as but not limited to one or more anti-sliding pads or non-slip structures. Preferably, the base 40 is provided with a placement hole 41 where a grinding unit GU can be placed to facilitate storage of the grinding unit GU.

The structural details of the pen-shaped nail filing device 10 of the present invention are described at greater length below with reference to FIG. 1, FIG. 2, and FIG. 3. The handle housing 11 includes a handle portion 111 and a front housing portion 112 detachably joined to the front end of the handle portion 111 so that not only can the dust accumulating in the pen-shaped nail filing device 10 be conveniently removed, but also the entire product can be assembled with ease. The front end of the front housing portion 112 has an opening 113 through which a grinding unit GU can be passed. The aforesaid position-limiting mechanism for tightening the claws 131 may be provided at, and on the inner side of, the opening 113. To make it easier for a user to grip the pen-shaped nail filing device 10, the front housing portion 112 or the handle portion 111 of the handle housing 11 may be provided with an anti-sliding member 15 so that the pen-shaped nail filing device 10 will not slip off easily after being held in a user's hand for a prolonged period of time. In one preferred embodiment, the anti-sliding member is provided on the front housing portion 112 due to ergonomic considerations given that one who is performing precision work with a pen-shaped object tends to hold a front end portion of the pen-shaped object. In one feasible embodiment, the anti-sliding member 15 is an anti-sliding pattern, an anti-sliding sleeve, or an anti-sliding material. The anti-sliding material may have any structural configuration that is commonly used to prevent sliding; the invention has no limitation in this regard. Preferably, the handle housing 11 is provided with a heat dissipation device (not shown) corresponding in position to the rotation speed-adjustable motor 30. The heat dissipation device may be a micro-fan or a plurality of heat dissipation fins; the invention has no limitation in this regard either.

The pen-shaped nail filing device 10 may be provided therein with various sensors for obtaining the corresponding parameter values of the pen-shaped nail filing device 10 respectively, thereby allowing the working mode of the pen-shaped nail filing device 10 to be detected and accessed in real time, and the control unit 21 to store various operation parameters into the storage unit either for future reference or in order to output a control instruction according to the parameters obtained.

In one feasible embodiment, the handle housing 11 or the master device 20 is provided therein with a rotation speed detection unit F1, although the rotation speed detection unit F1 may also be co-constructed with the rotation speed-adjustable motor 30 instead. The rotation speed detection unit F1 is connected or coupled to the control unit 21 in order to send the rotation speed parameter of the pen-shaped nail filing device 10 to the control unit 21 as feedback. The rotation speed detection unit F1 may be a sensor directly integrated into the rotation speed-adjustable motor 30. For example, a tachogenerator, a Hall transducer, an encoder, a current resistance compensator, a tachometer, or a pulse generator triggered by blockage of light may be used to convert rotation speed into an electrical signal as feedback. In another feasible embodiment, the rotation speed detection unit F1 may be a sensor that is separately provided in order to obtain the rotation speed parameter through, for example, a gear- or bushing-based linkage; the present invention has no limitation in this regard.

In another feasible embodiment, the handle housing 11 or the master device 20 is provided therein with a temperature detection unit F2, although the temperature detection unit F2 may also be co-constructed with the rotation speed-adjustable motor 30 instead. The temperature detection unit F2 is connected or coupled to the control unit 21 in order to send a temperature parameter of the pen-shaped nail filing device 10 to the control unit 21 as feedback. In one feasible embodiment, the temperature detection unit F2 may be a thermocouple, a resistance-based temperature sensor, or a thermistor; the present invention has no limitation in this regard. The temperature detection unit F2 sends the temperature parameter to the control unit 21 as feedback so that when the temperature parameter exceeds a preset threshold value, the control unit 21 will either issue a warning by outputting a control instruction to a human-machine interface or cut off the power supply. Thus, the temperature detection unit F2 provides an over-heat load monitoring function.

In another feasible embodiment, the handle housing 11 or the master device 20 is provided therein with a load detection unit F3, although the load detection unit F3 may also be co-constructed with the rotation speed-adjustable motor 30 instead. The load detection unit F3 is connected or coupled to the control unit 21 in order to send a load parameter of the pen-shaped nail filing device 10 to the control unit 21 as feedback. Here, the term "load" is not limited to the load resistance, load voltage or load current in a circuit; it can also refer to the reaction force acting on the rotation speed-adjustable motor 30 while the grinding unit GU mounted in the closable clamping member 13 is in operation. The load detection unit F3 may be implemented in many ways, one of which is by directly integrating a sensor, such as a torsion or torque sensor, into the rotation speed-adjustable motor 30 in order to detect the load on the rotation speed-adjustable motor 30 directly. In another feasible embodiment, the load is obtained by calculating through an algorithm, such as by converting the error between the anticipated output rotation speed (working power) and the actual output rotation speed (i.e., the sensor feedback) into a reaction force; the present invention has no limitation in this regard. The load parameter fed back from the load detection unit F3 is sent to the control unit 21 so that when the load parameter exceeds a preset threshold value, the control unit 21 will issue a warning by outputting a control instruction to a human-machine interface; thus, the load detection unit F3 provides an overload detection function. In another feasible embodiment, the control unit 21 is configured to record the user's operating habit by recording the values of the load parameter and provide operational suggestions (regarding, for example, the working power to be used, the rotation speed, and the force to be applied) based on the user's operating habit.

In another feasible embodiment, the handle housing 11 or the master device 20 is provided therein with a dust detection unit F4. The dust detection unit F4 is connected or coupled to the control unit 21 in order to send a dust amount parameter of the pen-shaped nail filing device 10 to the control unit 21 as feedback. In one feasible embodiment, the dust detection unit F4 may be a sensor for obtaining a dust gathering state by an optical measurement method, such as an infrared transducer or optical transducer capable of performing optical detection to obtain the amount or thickness of dust and so on and thereby determine the current dust gathering state. In another feasible embodiment, the dust detection unit F4 may be designed as an electrostatic sensor or electrical resistance sensor provided in the handle housing 11 at a position where dust tends to gather, so that the amount of dust can be known by detecting the accumulated amount of static electricity or the resistance between two points.

In another feasible embodiment, the handle housing 11 is provided therein with a connection detection unit F5, although the connection detection unit F5 may also be provided in the master device 20 instead. The connection detection unit F5 is connected or coupled to the control unit 21 in order to send an electrical parameter between the circuits of interest to the control unit 21 as feedback, thereby allowing the control unit 21 to derive a line connection state from the electrical parameter. More specifically, the connection detection unit F5 may be an impedance sensor, current sensor, or voltage sensor that can detect impedance, electric current, or voltage in order to determine whether the electrical contacts of interest are properly connected. In another feasible embodiment, the connection detection unit F5 may be a microswitch corresponding in position to the locking point of a component of interest so that when the component is locked to the locking point, the microswitch is triggered to confirm that the electrical connection has been properly made.

The following paragraphs describe an embodiment of the master device 20 in detail with reference to FIG. 1 to FIG. 3.

According to one feasible embodiment of the master device 20, a control instruction can be input into the master device 20 through a human-machine interface so as to control the working mode of the pen-shaped nail filing device 10 and of other related devices. The human-machine interface may be, but is not limited to, a multi-step/stepless turning knob (such as the turning knob 24 shown in FIG. 1 to FIG. 3), a geared knob, a control dial, a translational push lever, a wired or wireless transmission pedal, a touchpad, touch screen, touch button, press keys, a microphone, a multi-step/stepless trigger, or a multi-step/stepless regulation pushbutton; the present invention has no limitation in this regard.

The input interface of the master device 20 can provide a rotation speed modulation instruction to the control unit 21 of the master device 20 in order to control the working mode of the pen-shaped nail filing device 10, wherein the working mode includes the rotation direction of the grinding unit GU in use and the rotation speed and rotation direction of the rotation speed-adjustable motor 30. In addition, the input interface may be provided directly on the pen-shaped nail filing device 10 as a trigger, a push lever, a dial, or other similar mechanisms to enable adjustment of the rotation speed. More specifically, the rotation speed of the rotation speed-adjustable motor 30 may be controlled through analog-to-digital conversion or directly by a digital means; the present invention has no limitation in this regard.

The master device 20 may be connected to the pen-shaped nail filing device 10 by an electrical connection means. In one feasible embodiment, the electrical connection means EC may be conductive wires, coiled conductive wires, a cable box and its conductive wires, a circuit board, or a transmission cable; the present invention has no limitation in this regard.

To facilitate use, the master device 20 is preferably provided with a clip 25 on one side. The clip 25 allows a user to clip the master device 20 to a stationary object or carry the master device 20 around by clipping the master device 20 to the user's clothes so that the user can move freely while using the nail filing machine 100.

In one feasible embodiment, the master device 20 includes a display unit 26. The display unit 26 may display an indication of rotation speed, an indication of operation time, an indication of the remaining power level, an indication of load, an indication of forward/reverse rotation, an indication of temperature, or an indication of the line connection state so that a user can know the current working state from the indication displayed. The present invention has no limitation on the content displayed by the display unit 26. In one feasible embodiment, the display unit 26 may be implemented as an indicator light, a digital display, a liquid crystal display, a touch-controlled display, an electronic-paper display, or a projection display; the invention has no limitation in this regard either.

In one feasible embodiment, the master device 20 includes a rechargeable battery 27 and/or a power supply unit 22 that is connected or coupled to the control unit 21 in order to provide the control unit 21 with the electricity required for its operation. In one feasible embodiment in which an external adapter is used, the power supply unit 22 may be a voltage regulation circuit, a rectifier, an electrical filter, a protection circuit, or a circuit composed of a combination of the above; the present invention has no limitation in this regard. In embodiments where no external adapter is used, an electromagnetic interference (EMI) filter circuit, a power factor correction circuit, a main transformer, and so on may be used and arranged as needed in addition to a voltage regulation circuit, a rectifier, or an electrical filter; the invention has no limitation in this regard either. The rechargeable battery 27 may be, but is not limited to, a nickel-cadmium battery, a nickel-hydrogen battery, a lithium-ion battery, a lithium polymer battery, or a lithium iron phosphate battery.

In one feasible embodiment that includes the base 40, the base 40 is configured for use as a charger. In this embodiment, the base 40 is provided with a power supply 42 to be connected to an external power source and a power providing unit 43 connected to the power supply 42. The power providing unit 43 may be a physical electrical connection port or wireless charging module (e.g., a coil) that is directly connected or coupled to a power port 28 (e.g., a physical power port or a wireless power receiving side) of the master device 20 in order to provide the rechargeable battery 27 and/or the power supply unit 22 with the required electricity. In one feasible embodiment, the base 40 may also serve as an expansion unit, with one or a plurality of expansion ports (not shown) provided on the base 40 to transmit electric power or signal through specific terminals. When the nail filing machine 100 is connected to an expansion device (be it made by an original equipment manufacturer, an original design manufacturer, an original equipment supplier, or an aftermarket supplier), the master device 20, the specific terminals of the corresponding expansion port, and the control chip (or communication chip) in the base 40 will be able to identify the expansion device by its type, provide a control instruction corresponding to the type of the expansion device, and transmit the control instruction to the control unit 21 of the master device 20 in order to coordinate simultaneous or separate operations of the nail filing machine 100 and the expansion device; the present invention has no limitation on whether the nail filing machine 100 and the expansion device should work simultaneously or separately. Any one or all of the master device 20, the specific terminals of the corresponding expansion port, and the control chip in the base 40 may be configured to transmit the control instruction; the invention has no limitation in this regard either. Moreover, the one or more expansion ports may supply electricity through specific power terminals; for example, the power supply 42 may be connected or coupled to the one or more expansion ports in order to supply electricity thereto and thereby recharge the one or more specific devices connected respectively to the one or more expansion ports.

In one feasible embodiment, the master device 20 includes a timer 23 for recording the working time of the rotation speed-adjustable motor 30. The timer 23 may also record the working time of the rechargeable battery 27 in order for the control unit 21 to calculate the remaining service life of the rechargeable battery 27 according to the working time of the rechargeable battery 27 or the number of times of charging and discharge. As mentioned above, the control unit 21 records the rotation speed parameter and, when the working time of a particular rotation speed parameter exceeds a preset value, stores that rotation speed parameter into the storage unit as an entry in the frequently-used-parameter list, thereby recording the user's frequently used rotation speed. In one feasible embodiment, the timer 23 may be a separate chip or directly integrated into the control unit 21; the present invention has no limitation in this regard.

The present invention may further incorporate an ultraviolet (UV) light sterilization container for sterilizing the grinding units. Please refer to FIG. 7 and FIG. 8 for two structural diagrams of the UV light sterilization container of the invention.

Figure 7:
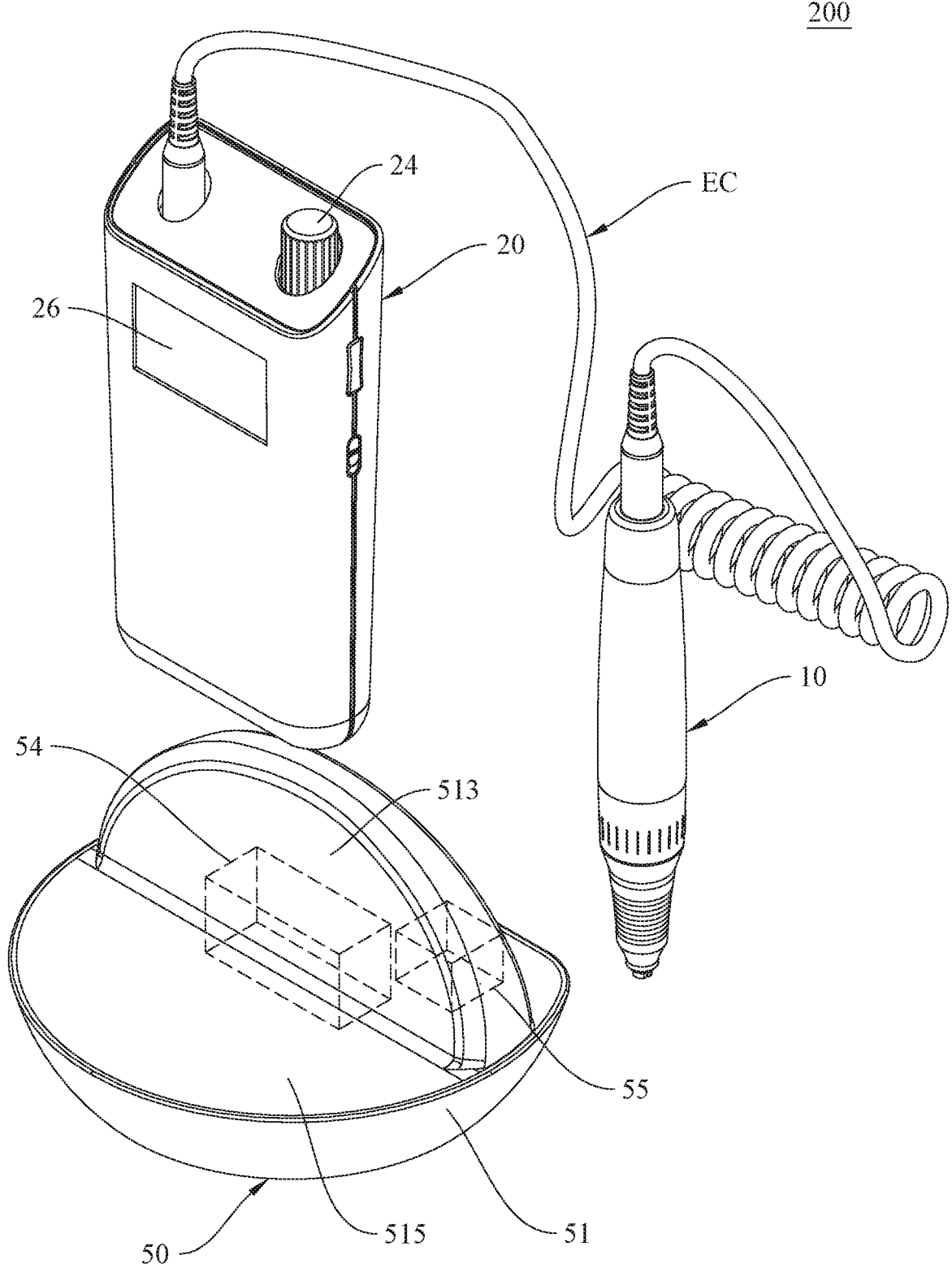
FIG. 7 is a first structural diagram of the UV light sterilization container of the present invention.
Figure 8:
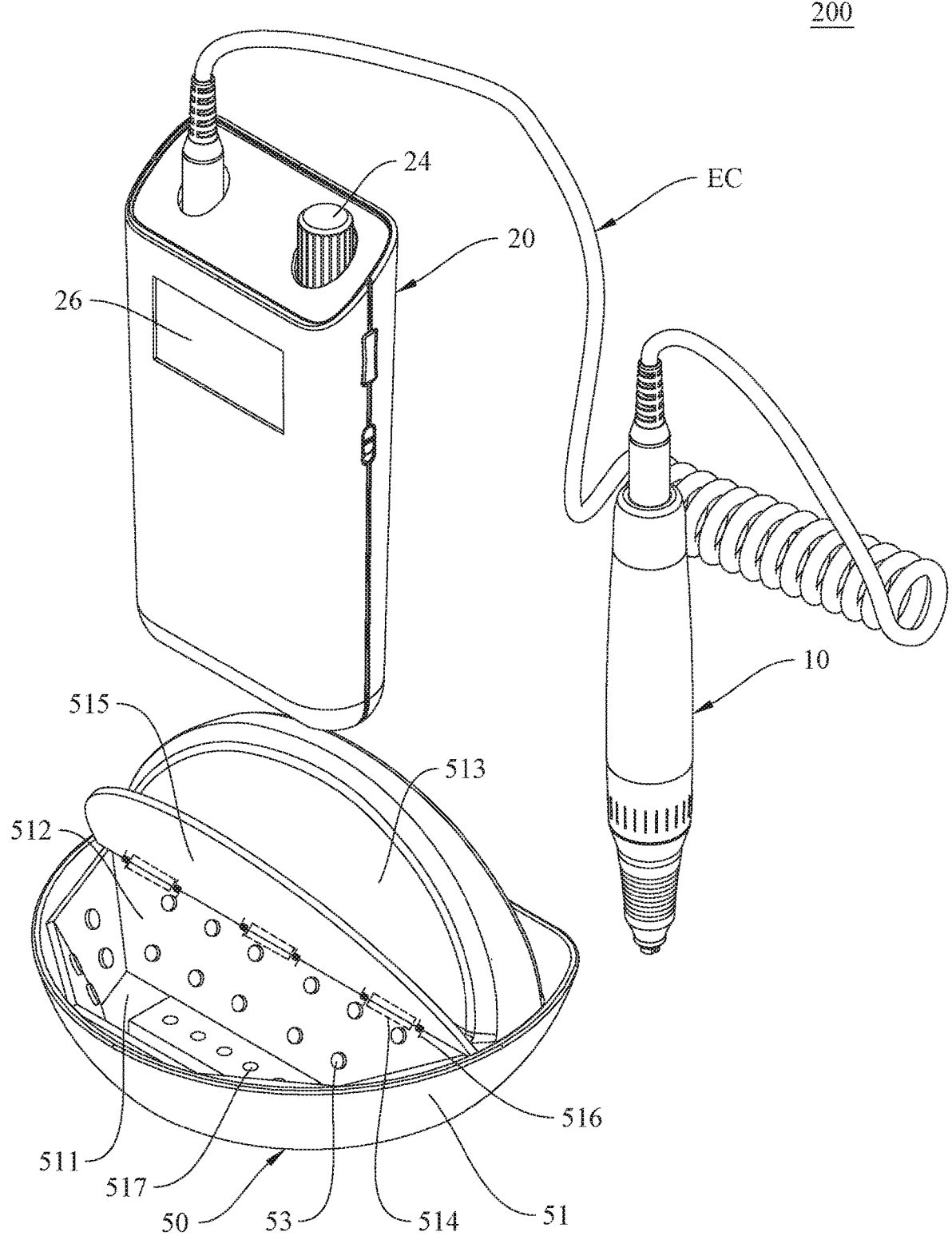
FIG. 8 is a second structural diagram of the UV light sterilization container of the present invention.

As shown in FIG. 7 and FIG. 8, the UV light sterilization container 50 of the present invention includes a housing 51, a power source module 55, one or a plurality of UV light emitting units 53, and a control module 54. The housing 51 has a receiving space 511. A plurality of placement units 517 where a plurality of grinding units GU can be respectively placed are provided in the receiving space 511. In one feasible embodiment, the placement units 517 may be vertical or horizontal grooves. The vertical grooves may correspond in shape to the bottom portions of the grinding units GU so that each grinding unit GU can be easily inserted into one of the vertical grooves to receive 360° sterilization. Similarly, the horizontal grooves may correspond in shape to a lateral portion of each grinding unit GU to facilitate one-sided sterilization of the grinding units GU. In one preferred embodiment, the placement units 517 are grooves formed in a transparent frame so that the inserted, and hence covered, portion of each grinding unit GU inserted in one of the grooves can still receive and be sterilized by UV radiation. The invention has no limitation on the configuration of the placement units 517.

In one feasible embodiment, the UV light sterilization container 50 may be externally connected or coupled to the master device 20 or the base 40 of the nail filing machine. For example, the UV light sterilization container 50 may be electrically connected to the base 40 or the master device 20 of the nail filing machine 100 by conductive wires or a wireless power source module in order to receive the electricity required to activate the UV light sterilization container 50. It is understood that the UV light sterilization container 50 may also include a power supply module and be powered by an independent source of mains electricity. In another feasible embodiment, the UV light sterilization container 50 may be co-constructed with the base 40 or the master device 20 of the nail filing machine 100. In the embodiment shown in FIG. 7 and FIG. 8, the UV light sterilization container 50 is co-constructed with the base 40.

The housing 51 of the UV light sterilization container 50 has one or a plurality of reflective surfaces 512 (or reflective units such as mirrors) on the inner side, i.e., the side facing the receiving space 511. The reflective surfaces 512 can reflect the UV light of the UV light emitting units 53 through the receiving space 511 and thereby direct the UV light to each grinding unit GU placed in the receiving space 511, allowing the UV light to work sufficiently on each grinding unit GU. In one feasible embodiment, the housing 51 of the UV light sterilization container 50 may be made of a photochromic material such that each time the UV light sterilization container 50 is activated, the housing 51 changes color to produce a color changing effect. In one preferred embodiment, the housing 51 may have a normal transparent or translucent state and a UV-blocking state that takes place only when the UV light emitting units are activated, the objective being to block UV light effectively when the UV light emitting units 53 are activated, thereby protecting the user's eyes from injury by the UV light.

The housing 51 includes a main body portion 513 and a cover 515 that is pivotally provided on the main body portion 513 via an elastic opening/closing means 514. In one feasible embodiment, the elastic opening/closing means 514 may be a spring, an elastic plate provided on a hinge, or other elastic components; the present invention has no limitation in this regard. To extend the service life of the cover 515, one feasible embodiment is so designed that the cover 515 is pivotally provided on the main body portion 513 through a damper unit 516, wherein the damper unit 516 may be a gear-based or pneumatic damping hinge to slow down the opening/closing of the cover 515, lest the cover 515 or the hinge itself be damaged by a rapid springing-open/springing-close action of the cover.

Apart from the embodiments described above, the present invention may also involve the use of a mobile device. Please refer to FIG. 9 for a block diagram of the nail filing system of the invention.

Figure 9:
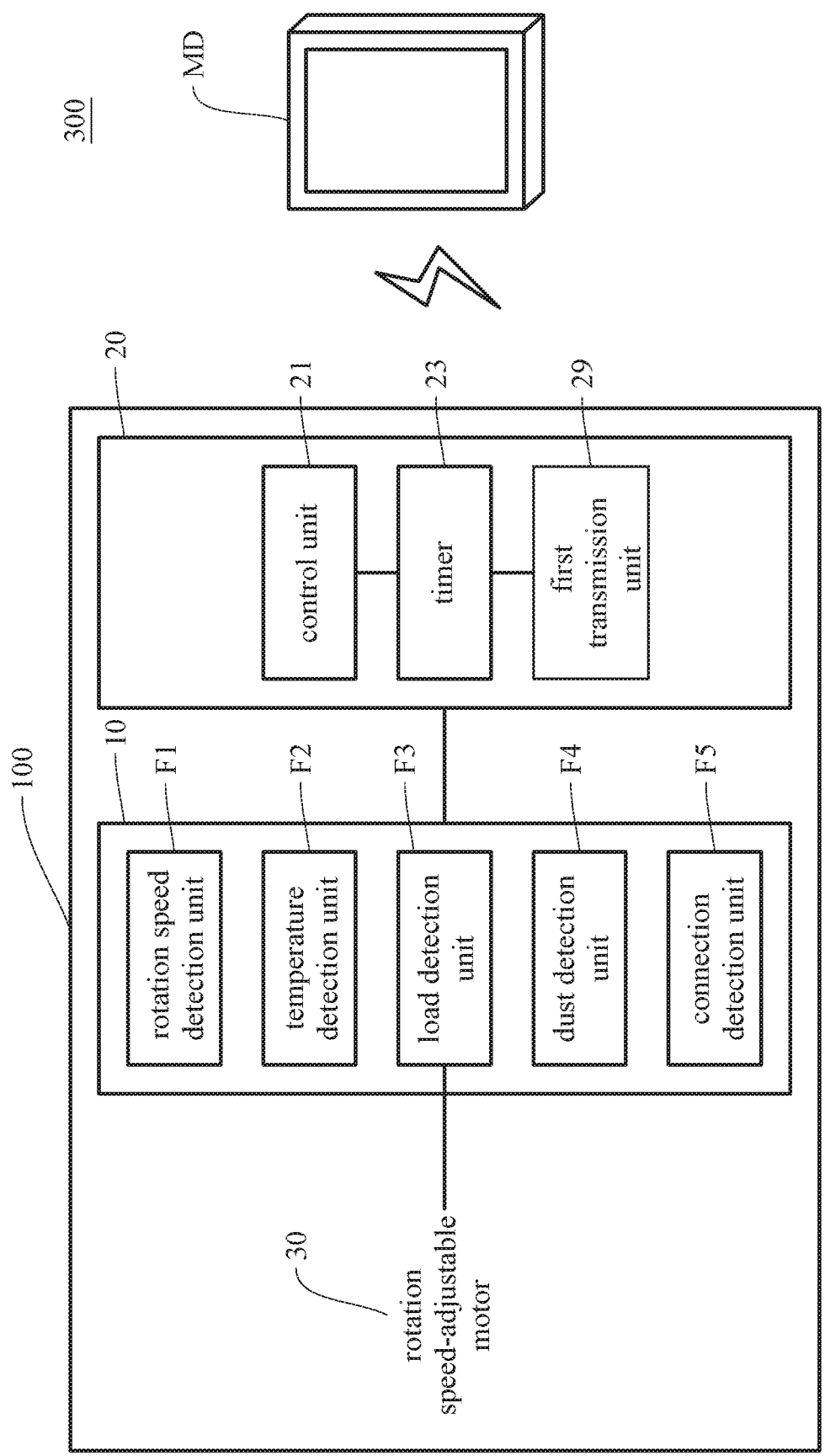
FIG. 9 is a block diagram of the nail filing system of the present invention.

The embodiment shown in FIG. 9 discloses a nail filing system 300 that includes the nail filing machine 100 of the present invention and a mobile device MD that is connected to the nail filing machine 100 by a transmission means. In this embodiment, the master device 20 of the nail filing machine 100 further includes a first transmission unit 29 connected to the control unit 21, and the mobile device MD is connected to the first transmission unit 29 of the nail filing machine 100 through a second transmission unit (not shown) in order to access the data in the control unit 21 via the first transmission unit 29.

The transmission means and the transmission units may be based on a wireless or wired transmission method, such as wireless transmission (e.g., Wi-Fi) or transmission through physical conductive wires (e.g., electrical wiring); the present invention has no limitation in this regard.

The mobile device MD can work with the pen-shaped nail filing device 10 in order to access the parameters obtained by the control unit 21 through the rotation speed detection unit F1, the temperature detection unit F2, the load detection unit F3, the dust detection unit F4, and the connection detection unit F5; record those parameters into the database in the mobile device; and perform the control procedure corresponding to each parameter. The feasible embodiment hereby has the rotation speed detection unit F1, the temperature detection unit F2, the load detection unit F3, the dust detection unit F4, and the connection detection unit F5 provided in the pen-shaped nail filing device 10; however, the rotation speed detection unit F1, the temperature detection unit F2, the load detection unit F3, the dust detection unit F4, and the connection detection unit F5 can also be provided in the master device 20 or co-constructed with the rotation speed-adjustable motor 30 as well.

In one feasible embodiment, the mobile device MD can obtain the rotation speed parameter of the rotation speed-adjustable motor 30 through the control unit 21 and store the rotation speed parameter in a database format into the work history database in the storage unit of the mobile device MD.

In one feasible embodiment in which the master device 20 includes the timer 23 for recording the working time of the rotation speed-adjustable motor 30, the mobile device MD obtains the working time of the rotation speed-adjustable motor 30 through the control unit 21 and stores the working time into the work history database in the storage unit of the mobile device MD.

In one feasible embodiment, the mobile device MD obtains through the control unit 21 the temperature parameter of the rotation speed-adjustable motor 30 in the working state and stores the temperature parameter in a database format into the storage unit of the mobile device MD; and, when the temperature parameter exceeds a preset value, outputs a notification signal through the screen or the loudspeaker of the mobile device MD.

In one feasible embodiment, the mobile device MD obtains through the control unit 21 the load parameter of the rotation speed-adjustable motor 30 in the working state and, when the load parameter exceeds a safety value, outputs a notification signal through the screen or the loudspeaker of the mobile device MD.

In one feasible embodiment, the mobile device MD obtains the dust amount parameter through the control unit 21 and, when the dust amount parameter exceeds a preset value, outputs a notification signal through the screen or the loudspeaker of the mobile device MD.

In one feasible embodiment, the mobile device MD obtains the line connection state through the control unit 21 and, when the line connection state is an improper connection state, outputs a notification signal through the screen or the loudspeaker of the mobile device MD.

The notification signals serve a prompting purpose: they not only can prompt the user to take safety measures, but also can remind the user to perform maintenance work on or repair the nail filing machine 100; the present invention has no limitation on the action that a notification signal may prompt a user to take. For example, the screen of the mobile device MD may display an image signal, such as flashing light or words that directly pop up to show the message to take note of; or the loudspeaker of the mobile device MD may send out a sound signal, such as a repeated instruction sound or an artificial voice that carries the message to take note of; or the screen and the loudspeaker may display or send out an image signal and a sound signal at the same time. The present invention has no limitation on how the notification signals are issued.

In one feasible embodiment, the mobile device MD obtains the working time of the rotation speed-adjustable motor 30 through the control unit 21 and stores the working time in a database format into the storage unit of the mobile device MD.

The mobile device MD may output the rotation speed parameter and the temperature parameter as charts in order for a user to analyze their use habit. Or the mobile device MD may directly output an instruction shortcut according to a user's frequently used rotation speed so that the user can rapidly call the pre-stored frequently used rotation speed; in that case, the mobile device MD produces the effect of a user-friendly interface.

The mobile device MD may have application programs for directly controlling the working modes of the pen-shaped nail filing device 10, the master device 20, and the UV light sterilization container 50 so as to achieve multiplexing.

In one feasible embodiment, the control unit of the master device comprises a programmable controller, the mobile device provides a modification platform to a human-machine interface of the mobile device through a mobile application program installed in the processor of the mobile device, and the processor outputs a programming instruction according to the instruction input through the modification platform and sends the programing instruction to the control unit of the nail filing machine by a transmission means in order to modify the procedures of the control unit, wherein the transmission means may be wireless or wired transmission without limitation. In terms of actual operation, the mobile device may work in the following manner by way of example. To begin with, the human-machine interface of the mobile device may display a standby interface, a selection interface, or a working mode interface of the pen-shaped nail filing device. The selection interface allows a user to set the operation parameters or select from preset operation parameter modules. For example, the user may set, through the selection interface, the rotation speed required by a specific grinding member, or when the pen-shaped nail filing device is equipped with that specific grinding member, the selection interface may display the required rotation speed to facilitate selection by the user. The parameter modules may include not only the rotation speeds of grinding members, but also the magnitudes of the sound signal of the loudspeaker, different imported music files, the brightness levels of the screen, the resolutions of the screen, and so on; the present invention has no limitation in this regard. The working mode interface displays the state in which the pen-shaped nail filing device is being used, e.g., a certain grinding member is being used for filing at a certain rotation speed, or the rotation speed-adjustable motor is at a certain temperature and has been used for filing for a certain amount of time. The working mode interface and the selection interface may coexist so that a user can change the settings of the nail filing machine during use.

The mobile device may be, but is not limited to, a mobile phone, a tablet computer, a smart watch, or smart glasses.

The mobile application program may be common application program software compatible with the mobile device, such as a mobile application (app); the present invention has no limitation in this regard.

In summary, the present invention aims to provide a multifunctional nail filing machine, an ultraviolet (UV) light sterilization container, and a nail filing system including the nail filing machine. It is desirable that the nail filing machine can record a user's use habit and perform various functions so as to provide much better user experience than the prior art.

The above is the detailed description of the present invention. However, the above is merely the preferred embodiment of the present invention and cannot be the limitation to the implement scope of the invention, which means the variation and modification according to the present invention may still fall into the scope of the invention.

What is claimed is:

1. A nail filing machine, comprising:
a pen-shaped nail filing device including a handle housing and a main shaft provided in the handle housing, wherein the main shaft is provided with a closable clamping member; a master device separated from or co-constructed with the pen-shaped nail filing device, wherein the master device is connected or coupled to the pen-shaped nail filing device through an electrical connection, and the master device includes a control unit, the control unit includes a storage unit; and a rotation speed-adjustable motor provided in the handle housing or the master device, wherein the rotation speed-adjustable motor is connected or coupled to the main shaft in order to drive the main shaft into rotation; wherein the control unit adjusts a working mode of the pen-shaped nail filing device according to a corresponding control instruction, and the control unit sets a working mode for the pen-shaped nail filing device; wherein, the working mode comprises a manual control instruction in a manual setting list, a recorded control instruction in a frequently-used-parameter list, or a default control instruction in the storage unit; wherein, the manual control instruction in the manual setting list is set from the control unit according to an instruction input through a human-machine interface in order to record the manual control instruction into the storage unit, the recorded control instruction in the frequently-used-parameter list is recorded by the control unit with a rotation speed parameter when a working time of a certain rotation speed parameter exceeds a preset value, and the default control instruction is a preset control instruction already stored in the storage unit, and the control unit is configured to record a user's operating habit by recording values of a load parameter of the pen-shaped nail filing device and provide operational suggestions based on the user's operating habit.

2. The nail filing machine of claim 1, wherein the pen-shaped nail filing device includes a grinding unit mounted on the closable clamping member.

3. The nail filing machine of claim 1, wherein the rotation speed-adjustable motor is a bi-directional motor whose rotation direction is switched on an instruction of the control unit.

4. The nail filing machine of claim 1, wherein the handle housing is provided with a rotating member, wherein the closable clamping member is closed when the rotating member is turned in a direction, and the closable clamping member is opened when the rotating member is turned in an opposite direction.

5. The nail filing machine of claim 1, wherein the handle housing includes a handle portion and a front housing portion joined to a front end of the handle portion, and the front housing portion has a front end having an opening through which a grinding unit can be passed.

6. The nail filing machine of claim 1, wherein the handle housing has an outer side provided with an anti-sliding member.

7. The nail filing machine of claim 6, wherein the anti-sliding member is an anti-sliding pattern, an anti-sliding sleeve, or an anti-sliding material.

8. The nail filing machine of claim 1, wherein the handle housing is provided with a heat dissipation device corresponding in position to the rotation speed-adjustable motor.

9. The nail filing machine of claim 1, wherein the master device inputs a corresponding rotation speed modulation instruction to the control unit of the master device through a human-machine interface so as to control the working mode, and the working mode includes rotation speed and rotation direction of the rotation speed-adjustable motor.

10. The nail filing machine of claim 9, wherein the human-machine interface is a multi-step/stepless turning knob, a geared knob, a control dial, a translational push lever, a wired or wireless transmission pedal, a touchpad, touch screen, touch button, press keys, a microphone, a multi-step/stepless trigger, or a multi-step/stepless regulation pushbutton.

11. The nail filing machine of claim 1, wherein the master device is provided with a clip on one side.

12. The nail filing machine of claim 1, wherein the master device includes a rechargeable battery and/or a power supply unit that is connected or coupled to the control unit in order to provide the control unit with electricity required for its operation.

13. The nail filing machine of claim 12, further including a base where the master device can be placed.

14. The nail filing machine of claim 13, wherein the base has a bottom side provided with one or more anti-sliding pads or non-slip structures.

15. The nail filing machine of claim 13, wherein the base is provided with a power supply to be connected to an external power source and a power providing unit connected to the power supply, and the power providing unit is connected or coupled to a power port of the master device in order to provide the rechargeable battery and/or the power supply unit with required electricity.

16. The nail filing machine of claim 15, wherein the base is provided with one or more expansion ports, and the power supply is connected or coupled to the one or more expansion ports in order to supply electricity thereto.

17. The nail filing machine of claim 13, wherein the base is provided with a placement hole where a grinding unit can be placed.

18. The nail filing machine of claim 12, wherein the master device includes a timer for recording a working time of the rechargeable battery in order for the control unit to calculate a remaining service life of the rechargeable battery according to the working time of the rechargeable battery or a number of times of charging and discharge.

19. The nail filing machine of claim 1, wherein the master device includes a display unit displaying at least one indication selected from the group of rotation speed, operation time, remaining power level, load, forward/reverse rotation, temperature, and line connection state.

20. The nail filing machine of claim 1, wherein the electrical connection conductive wires, coiled conductive wires, a cable box and its conductive wires, a circuit board, or a transmission cable.

21. The nail filing machine of claim 1, wherein the handle housing of the pen-shaped nail filing device or the master device is provided therein with a rotation speed detection unit, or a rotation speed detection unit is co-constructed with the rotation speed-adjustable motor instead; wherein the rotation speed detection unit is connected or coupled to the control unit in order to send a rotation speed parameter of the pen-shaped nail filing device to the control unit as feedback.

22. The nail filing machine of claim 1, wherein the master device includes a timer for recording a working time of the rotation speed-adjustable motor.

23. The nail filing machine of claim 1, wherein the handle housing of the pen-shaped nail filing device or the master device is provided therein with a temperature detection unit, or a temperature detection unit is co-constructed with the rotation speed-adjustable motor instead; wherein the temperature detection unit is connected or coupled to the control unit in order to send a temperature parameter of the pen-shaped nail filing device to the control unit as feedback.

24. The nail filing machine of claim 1, wherein the handle housing of the pen-shaped nail filing device or the master device is provided therein with a load detection unit, or a load detection unit is co-constructed with the rotation speed-adjustable motor instead; wherein the load detection unit is connected or coupled to the control unit in order to send load parameter of the pen-shaped nail filing device to the control unit as feedback.

25. The nail filing machine of claim 1, wherein the handle housing of the pen-shaped nail filing device or the master device is provided therein with a dust detection unit, and the dust detection unit is connected or coupled to the control unit in order to send a dust amount parameter of the pen-shaped nail filing device to the control unit as feedback.

26. The nail filing machine of claim 1, wherein the handle housing of the pen-shaped nail filing device is provided therein with a connection detection unit, or a connection detection unit is provided in the master device instead; wherein the connection detection unit is connected or coupled to the control unit in order to send an electrical parameter between circuits of interest to the control unit as feedback, thereby allowing the control unit to derive a line connection state from the electrical parameter.

27. A nail filing system, comprising:
the nail filing machine of claim 1, wherein the nail filing machine further includes a first transmission unit connected to the control unit; and
a mobile device connected to the first transmission unit of the nail filing machine through a transmission means in order to access data in the control unit through the first transmission unit.

28. The nail filing system of claim 27, wherein the handle housing of the pen-shaped nail filing device or the master device is provided therein with a rotation speed detection unit, or a rotation speed detection unit is co-constructed with the rotation speed-adjustable motor instead; wherein the rotation speed detection unit is connected or coupled to the control unit in order to send a rotation speed parameter of the pen-shaped nail filing device to the control unit as feedback, and the mobile device obtains the rotation speed parameter of the rotation speed-adjustable motor through the control unit.

29. The nail filing system of claim 27, wherein the master device includes a timer for recording a working time of the rotation speed-adjustable motor, and the mobile device obtains the working time of the rotation speed-adjustable motor through the control unit.

30. The nail filing system of claim 27, wherein the handle housing of the pen-shaped nail filing device or the master device is provided therein with a temperature detection unit, or a temperature detection unit is co-constructed with the rotation speed-adjustable motor instead; wherein the temperature detection unit is connected or coupled to the control unit in order to send a temperature parameter of the pen-shaped nail filing device to the control unit as feedback, and the mobile device obtains the temperature parameter of the rotation speed-adjustable motor in a working state through the control unit.

31. The nail filing system of claim 27, wherein the handle housing of the pen-shaped nail filing device or the master device is provided therein with a load detection unit, or a load detection unit is co-constructed with the rotation speed-adjustable motor instead; wherein the load detection unit is connected or coupled to the control unit in order to send a load parameter of the pen-shaped nail filing device to the control unit as feedback, and the mobile device obtains the load parameter of the rotation speed-adjustable motor in a working state through the control unit.

32. The nail filing system of claim 27, wherein the handle housing of the pen-shaped nail filing device or the master device is provided therein with a dust detection unit, the dust detection unit is connected or coupled to the control unit in order to send a dust amount parameter of the pen-shaped nail filing device to the control unit as feedback, and the mobile device obtains the dust amount parameter through the control unit.

33. The nail filing system of claim 27, wherein the handle housing of the pen-shaped nail filing device is provided therein with a connection detection unit, or a connection detection unit is provided in the master device instead; wherein the connection detection unit is connected or coupled to the control unit in order to send an electrical parameter between circuits of interest to the control unit as feedback, thereby allowing the control unit to derive a line connection state from the electrical parameter, and the mobile device obtains the line connection state through the control unit.

34. The nail filing system of claim 27, wherein the control unit of the pen-shaped nail filing device comprises a programmable controller, the mobile device provides a modification platform to a human-machine interface of the mobile device through a mobile application program installed in a processor of the mobile device, and the processor outputs a programming instruction according to an instruction input through the modification platform and sends the programing instruction to the control unit of the nail filing machine by a transmission means in order to modify procedures of the control unit.

* * * * *